United States Patent [19]

Garcia et al.

[11] Patent Number: 5,494,895
[45] Date of Patent: Feb. 27, 1996

[54] SCORPION PEPTIDE MARGATOXIN WITH IMMUNOSUPPRESSANT ACTIVITY

[75] Inventors: Maria L. Garcia, Edison; Gloria C. Koo, Woodbridge; Reid J. Leonard, Westfield; Chiu-Chuan S. Lin, Holmdel; Robert S. Slaughter, Chatham; Scott P. Stevens, Westfield; Joanne M. Williamson, Cranford, all of N.J.

[73] Assignee: Merck & Co., Inc., Rahway, N.J.

[21] Appl. No.: 96,942

[22] Filed: Jul. 22, 1993

[51] Int. Cl.⁶ .......................... A61K 38/17; C07K 14/435
[52] U.S. Cl. .......................... 514/12; 530/324; 424/278.1; 930/260; 435/69.1
[58] Field of Search .......................... 514/2, 12; 530/324, 530/300; 424/1.1, 278.1; 930/260; 435/69.1

[56] References Cited

U.S. PATENT DOCUMENTS

| | | | |
|---|---|---|---|
| 4,929,718 | 5/1990 | Possani et al. | 530/324 |
| 4,960,867 | 10/1990 | Garcia et al. | 530/324 |
| 5,006,512 | 4/1991 | Ohnishi | 514/2 |

OTHER PUBLICATIONS

Park et al, *PNAS* 88:2046–2050 (Mar. 1991).
Park et al, "Design, synthesis, and functional expression of a gene for charybdotoxin . . . " PNAS 88(6):2046–2050 (1991); abstract #118447 in *Biol. Abst.* 91(11):AB–458 (Jun. 1991).
Possani et al "The Primary Structure of Noxiustoxin . . . " *Carlsberg Res. Commun.* 47: 285–289 (1982).
R. J. Leonard et al., "Selective Blockers of Voltage-gated K channels depolarize human T lymphocytes Mechanism of the antiproliferative effect of charybdotoxin," Proc. Natl Acad. Sci. vol. 89:, pp. 10094–10098 (Nov. 1992).
C. S. Lin et al., "Voltage-gated Potassium Channels Regulate Calcium-dependent Pathways Involved In Human T-Lymphocyte Activation" J. Exp. Med., vol. 177: pp. 637–644, (Mar. 1993).
K. G. Chandy et al., "Voltage–Gated Potassium Channels Are Required For Human T Lymphocyte Activation", J. Exp. Med., vol. 160:, pp. 369–385 (1984).
DeCoursey et al., "Voltage–gated K Channels In Human T Lymn Mitogenesis?", Nature, vol. 307., pp. 465–468 (1984).
J. Novick et al., "Purification & Characterization of Two Novel Peptidyl Toxins Directed against K Channels from Venom of New World Scorpions" Poster Presentation, Feb. 25, 1991.
M. Price et al., "Charybdotoxin Inhibits Proliferation & Interleukin 2 Production in Human Peripheral Blood Lymphocytes", Proc. Natl. Acad. Sci. USA, vol. 86:, pp. 10171–10175 (Dec. 1989).
J. Vazquez, "Characterization of High Affinity Binding Sites for Charybdotoxin in Synaptic Plasma Membranes from Rat Brains", J. Biol Chem, vol. 256:, pp. 15564–15571 (1990).
M. Garcia–Calvo, "Purification, Characterication, & Biosynthesis of Margatoxin, A Component of Centruroides Margaritatus Venom That Selectively Inhibits Voltage–dependent Potassium Channels", J. Biol. Chem., vol. 268:, pp. 118866–18874 (Jul. 1993).
J. Novick et al., "Purification & Characterization of 2 Novel Peptidyl Toxins directed Against K Channels From Venom of New World Scorpions" Biophys J, vol. 59, p. 78a (1991) (Abstr.) #124.
R. Leonard et al., "K Channels In Human T–Cells (HTC); Regulation of Membrane Potential." Biophys. J. vol. 61: Abstract, p. A380. (1992) (Abstr.) #2187.
R. S. Slaughter et al., "Inhibition by Toxins of Charybdotoxin Binding To The Voltage–Gated Potassium Channel of Lymphocytes: Correlation with Block of Activation of Human Peripheral T–Lymphocytes." Biophys J., vol. 59:, p. 213a (1991) (abstr.) #TuPM–A2.

*Primary Examiner*—Stephen G. Walsh
*Attorney, Agent, or Firm*—Francis P. Bigley; Mark R. Daniel

[57] ABSTRACT

A thirty-nine amino acid peptide, Margatoxin (MgTX), is purified to homogeneity from venom of the scorpion *Centruroides margaritatus*. The gene encoding MgTX is constructed and this gene is expressed in *E. coli*, to produce recombinant MgTX. MgTX is a potent and selective inhibitor of a voltage-dependent K⁺ channel present in human lymphocytes. MgTX exhibits immunosuppressant activity with human T-lymphocytes, and is useful as an immunosuppressant, in modeling nonpeptidyl K⁺ channel blockers, and in establishing biochemical assays based on ligand binding or other protocols with which to screen for other novel modulators of voltage dependent K⁺ channels in lymphocytes and other tissues including the brain. As an immunosuppressant, MgTX is useful in the treatment of autoimmune diseases, the prevention of rejection of foreign organ transplants and/or related afflictions, diseases and illnesses.

9 Claims, 1 Drawing Sheet

FIG-1

SCORPION PEPTIDE MARGATOXIN WITH IMMUNOSUPPRESSANT ACTIVITY

SUMMARY OF THE INVENTION

A thirty-nine amino acid peptide, Margatoxin (MgTX), is purified to homogeneity from venom of the scorpion *Centruroides margaritatus*. The gene encoding MgTX is constructed, and this gene is expressed in *E. coli* to produce recombinant MgTX. MgTX is a potent and selective inhibitor of a voltage-dependent $K^+$ channel present in human lymphocytes. MgTX exhibits immunosuppressant activity with human T-lymphocytes, and is useful as an immunosuppressant, in modeling nonpeptidyl $K^+$ channel blockers, and in establishing biochemical assays based on ligand binding or other protocols with which to screen for other novel modulators of voltage dependent $K^+$ channels in lymphocytes and other tissues including the brain. As an immunosuppressant, MgTX is useful in the treatment of autoimmune diseases, the prevention of rejection of foreign organ transplants and/or related afflictions, diseases and illnesses.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's and corticosteroids act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A, which was approved by the US FDA in 1983, is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting fewer side effects are constantly being searched for in the field. The present invention provides for an immunosuppressant peptide that is a selective inhibitor of a voltage dependent potassium channel, $K_v1.3$, that is found on human T-lymphocytes.

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of $K^+$ channels, in their role as modulators of the plasma membrane potential in human T-lymphocytes, has been postulated to play a role in eliciting immunosuppressive responses. In regulating membrane potential, $K^+$ channels play a role in the regulation of intracellular $Ca^{++}$ homeostasis, which has been found to be important in T-cell activation. The biochemical characterization of $K^+$ channels is underdeveloped, due to the paucity of selective high affinity probes.

Functional voltage-gated $K^+$ channels can exist as multimeric structures formed by the association of either identical or dissimilar subunits. This phenomena is thought to account for the wide diversity of $K^+$ channels found in different tissues. Despite the rapid advances in the molecular biology of $K^+$ channels, subunit compositions of native $K^+$ channels and the physiologic role that particular channels play are, in most cases, still unclear. To address these problems, potent, selective probes for channels of interest must be identified.

The $K_v1.3$ channel is a voltage-gated potassium channel that is found in neurons, blood cells, osteoclasts and T-lymphocytes. The Chandy and Cahalan laboratories proposed a hypothesis that blocking the $K_v1.3$ channel would illicit an immunosuppressant response. (Chandy et al., J. Exp. Med. 160, 369, 1984; Decoursey et al., Nature, 307, 465, 1984). However, the $K^+$ channel blockers employed in their studies were non-selective. Until the present invention, no specific inhibitor of the $K_v1.3$ channel existed to test this hypothesis. Although a laboratory (Price et al., Proc. Natl. Acad. Sci. USA, 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{2+}$ activated $K^+$ channels) in human T lymphocytes, limiting the use of this toxin as a probe for the physiological role of $K_v1.3$ (Leonard et al., Proc. Natl. Acad. Sci. USA, 89, 10094, 1992). Since MgTX is a selective $K_v1.3$ inhibitor, it is useful to show that blocking of $K_v1.3$ will inhibit T cell activation (Lin et al., *J. Exp. Med*, 177, 637, 1993).

Scorpion venoms have been recognized as a source of peptidyl inhibitors of various types of $K^+$ channels. Some of these peptides have been purified to homogeneity and their properties characterized. A preliminary report describing the presence of a specific peptidyl voltage-gated potassium channel inhibitor in *C. margaritatus* venom that is homologous with NxTX has been made in abstract form (Novick, et al. (1991) *Biophys J* 59, 78). The most extensively studied of these toxins is charybdotoxin (ChTX). See U.S. Pat. No. 4,906,867. ChTX is a thirty-seven amino acid peptide isolated from venom of the old world scorpion *Leiurus quinquestriatus* var. *hebraeus*. Originally described as an inhibitor of the high-conductance, $Ca^{2+}$-activated $K^+$ (Maxi-K) channel present in muscle and neuro-endocrine cells, ChTX was later found also to inhibit a number of different medium- and small-conductance $Ca^{2+}$-activated $K^+$ channels, as well as a voltage-dependent $K^+$ channel ($K_v1.3$) In each case, channel inhibition occurs with similar potency, in the low nanomolar range. Therefore, caution has to be exercised when using ChTX to study the physiological role of a given channel in a tissue of interest. A related toxin, iberiotoxin (IbTX), shares 68% sequence homology with ChTX and selectively blocks the Maxi-K channel. Other peptidyl inhibitors, such as limbatustoxin (LbTX) and kaliotoxin (KTX), have also been shown to possess greater selectivity for the Maxi-K channel. Other peptidyl toxins homologous to ChTX have been identified (e.g., noxiustoxin.). Noxiustoxin is a high-affinity blocker of $K_v1.3$, but because it also inhibits the delayed rectifier $K^+$ channel of squid axon and the Maxi-K channel from skeletal muscle, and is not selective for $K_v1.3$, it is not a satisfactory probe of $K_v1.3$ channels.

Figure 1:
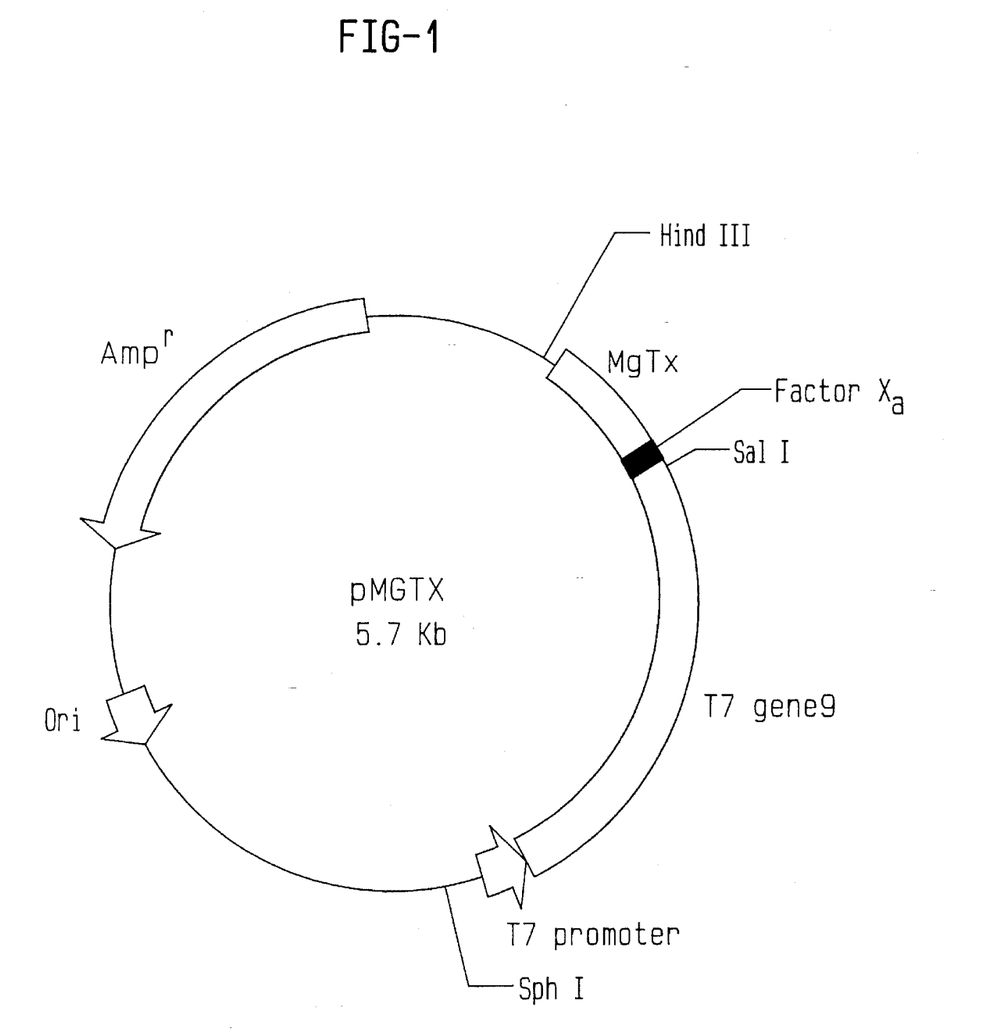
FIG. 1 depicts the plasmid map of the synthetic MgTX gene for expression in *E. coli*, the locations of the synthetic MgTX gene, Factor Xa cleavage site, and the T7 gene9 fusion protein. Amp$^r$ represents ampicillin resistance; Ori represents the origin.

The peptide of the present invention, MgTX, represents a unique tool with which to probe the function of $K_v1.3$. This channel has been identified as the major voltage-dependent $K^+$ conductance in peripheral human T-lymphocytes. Since human T-lymphocytes contain, in addition to $K_v1.3$, several distinct small-conductance $Ca^{2+}$-activated $K^+$ channels that are also blocked by ChTX, ChTX is inadequate for assigning the role of any specific channel in the control of T cell proliferation. MgTX has recently been demonstrated to depolarize human T cells (Leonard et al., *Proc. Natl. Acad. Sci. U.S.A.* 89, 10094, 1992) and to prevent activation and proliferation of these cells mediated by $Ca^{2+}$-dependent pathways (Lin et al., *J. Exp. Med.*, 177, 637, 1993).

fusion protein. Amp$^r$ represents ampicillin resistance; Ori represents the origin.

DETAILED DESCRIPTION OF THE INVENTION

The invention relates to Margatoxin (MgTX), a novel 39 amino acid peptide containing six cysteine residues and seven positively charged residues, derived from venom of the scorpion *Centruroides margaritatus:* (SEQ ID NO:1)

```
Thr—Ile—Ile—Asn—Val—Lys—Cys—Thr—Ser—Pro—Lys—Gln—Cys—Leu—Pro—Pro—
                5                    10                    15
Cys—Lys—Ala—Gln—Phe—Gly—Gln—Ser—Ala—Gly—Ala—Lys—Cys—Met—Asn—Gly—
              20                    25                    30
Lys—Cys—Lys—Cys—Tyr—Pro—His
              35
```

This invention relates to the purification of MgTX from *C. margaritatus* venom so that the peptide is substantially free from other peptide contaminants as judged by reversed phase HPLC, SDS-PAGE analysis, amino acid compositional analysis, N-terminal degradation sequence analysis, and electrospray mass spectroscopy. MgTX is useful as a selective probe for $K_v1.3$, and may be employed in a screen for other $K_v1.3$ inhibitors exhibiting immunosuppressant activity. Additionally, MgTX is useful in modeling studies to design nonpeptidyl $K_v1.3$ blockers. MgTX is also useful for its immunosuppressive activity. MgTX inhibits interleukin 2 production in human T-lymphocytes (Lin et al., *J. Exp. Med.* 177, 637, 1993).

This invention also relates to the construction of a gene encoding MgTX (SEQ ID NO:2) and the expression of this gene in *E. coli* to produce recombinant MgTX. The DNA sequence encoding MgTX is shown below: (SEQ ID NO:2)

```
5' ACCATCATCA ACGTTAAATG CACCTCTCCG AAACAGTGCC

TGCCGCCGTG CAAAGCTCAG TTCGGTCAGT CTGCTGGTGC

TAAATGCATG AACGGTAAAT GCAAATGCTA CCCGCACTGA 3'
```

Venom of the new world scorpion *Centruroides margaritatus* was determined to contain an activity selectively directed against voltage-dependent $K^+$ channels: it inhibited binding of [$^{125}$I]ChTX to $K_v1.3$ channels in rat brain synaptosomal membranes, but not to Maxi-K channels in smooth muscle sarcolemma. This invention comprises the purification, from this venom, of margatoxin (MgTX), its primary sequence and characterization as a $K_v1.3$ inhibitor, and the expression of recombinant MgTX in *E. coli*. MgTX is structurally related to other known $K^+$ channel blocking peptides, but is distinguished by its potent and selective blockade of $K_v1.3$. Given these properties, MgTX represents a useful tool for studying the physiologic role of $K_v1.3$. This invention also relates to the construction of a gene encoding MgTX and the expression of this gene in *E. coli* to produce recombinant MgTX.

It is also well-known that there is a substantial amount of redundancy in the various codons which code for specific amino acids. Therefore, this invention is also directed to those DNA sequences which contain alternative codons which code the identical amino acid. For purposes of this specification, a sequence bearing one or more replaced codons will be defined as a degenerate variation. Also included within the scope of this invention are variations in the DNA sequence which do not alter the ultimate physical properties of the expressed protein.

This invention also concerns systems for expressing MgTX. This system includes expression vectors which incorporate a base sequence encoding MgTX. This expression vector is then used to transfect a suitable expression host, preferably *E. coli*, which translates the genetic information, synthesizes the protein or partial protein and enables expression of the cloned MgTX. FIG. 1 depicts the plasmid map of the synthetic MgTX gene for expression in *E. coli*, the locations of the synthetic MgTX gene, Factor Xa cleavage site, and the T7 gene9 fusion protein.

Because the amounts of MgTX that can be obtained from scorpion venom are small, the ability to produce large amounts of peptide by recombinant techniques allows its application in assays to develop other potassium channel inhibitors. Radiolabeling of MgTX with $^{125}$I Na, or derivitization with [$^{125}$I] Bolton-Hunter reagent or with a biotin conjugate, allows the development of a binding assay to screen for either competitive or allosteric modulators of peptide binding that might possess $K_v1.3$ channel inhibitory activity. MgTX can also be used as a positive control in any functional assay to discover inhibitors of $K_v1.3$.

MgTX peptide is isolated from crude venom of the scorpion *C. margaritatus*. Preferably, lyophilized venom is employed. The lyophilized venom is suspended in a basic, low ionic strength buffer, pH 8 to 10, preferably 20 mM sodium borate buffer at pH 9.0 at a concentration of 5 mg/mL. The venom is agitated, preferably by vortex, and clarified, preferably by centrifugation at between 20,000×g to 30,000×g for about 10 to 20 minutes, most preferably at 27,000×g for 15 minutes. The supernatant is removed and preferably is filtered through 0.22 μm low protein binding filters made of hydrophilic DURAPORE (PVDF) membrane to remove particulates that would clog ion exchange systems, such as FPLC systems, preferably through a MILLEX-GV 0.22 μm filter, and loaded onto an ion exchange system, preferably an FPLC system in the buffer originally employed to dissolve the venom. Most preferably, the supernatant is loaded onto a MonoS FPLC column (HR5/5; PHARMACIA), equilibrated with 20 mM sodium borate, pH 9.0. Absorbance is measured at 280 nm. After the absorbance of the eluate returns to baseline, bound material is eluted from the resin by employing a salt gradient, preferably with a linear gradient of NaCl (0.75 M/hr) at a flow rate of 0.5 mL/min. Fractions are collected and separated and assayed for their activity against K$^+$ channels. Preferably, the ability of the fractions to inhibit [$^{125}$I]ChTX binding to either rat brain synaptic plasma membranes ($K_v1.3$ channels; Vazquez et al., *J. Biol. Chem.* 265, 15564, 1990) or bovine aortic smooth muscle sarcolemmal membranes (Maxi-K channels; Vazquez et al., *J. Biol. Chem.* 264, 20902, 1989) is measured. Fractions that block [$^{125}$I]ChTX binding to brain membranes and not to smooth muscle sarcolemmal membranes and that display the highest absorbance at 280 nm are loaded onto a reversed-phase HPLC system and eluted along a linear gradient. Preferably, the material is loaded onto a 300 Å pore size C$_{18}$ reversed phase HPLC column (0.46×25 cm) equilibrated with 10 mM trifluoroacetic acid (TFA) and eluted with a linear gradient of isopropyl alcohol/acetonitrile (2:1; 0–15%, 33 minutes) at a flow rate of 0.5 mL/min. Fractions are collected, lyophilized and reconstituted in a buffered aqueous medium, preferably 100 mM NaCl, 20 mM Tris-HCl, pH 7.4. Material exhibiting inhibitory binding activity against [$^{125}$I] ChTX binding to rat brain synaptic plasma membrane vesicles is identified.

To determine the molecular weight of the peptide, samples are denatured in the presence of SDS, applied to gels, and the active material is analyzed using silver staining to reveal the active component. Preferably, the material is applied to precast 16% Tricine gels (NOVEX).

The MgTX gene may be constructed by a variety of methods including, but not limited to, cloning of the gene from scorpion DNA or RNA extracts, using the DNA sequence disclosed herein and standard recombinant DNA techniques (See Maniatis Cold Spring Harbor). An alternative is to synthesize overlapping oligonucleotides, followed by annealing and extension of these oligonucleotides to produce a double-stranded DNA molecule encoding the peptide sequence of MgTX, together with flanking sequence necessary to accomplish insertion of the MgTX synthetic gene into a suitable expression plasmid. Preferably, the gene is constructed beginning with two synthetic oligonucleotides of the sequences below: (SEQ ID NO:3).

5' GTCGACGGAT CCATCGAAGG TCGTACCATC ATCAACGTTA

AATGCACCTC TCCGAAACAG TGCCTGCCGC CGTGCAAAGC TCAG 3'

(SEQ ID NO: 4)

5' GGCACGTTTC GAGTCAAGCC AGTCAGACGA CCACGATTTA

CGTACTTGCC ATTTACGTTT ACGATGGGCG TGACTATCCT TCGAA3'

These oligonucleotides may be synthesized using a commercial DNA synthesizer such as the ABI model 391 DNA Synthesizer (Applied Biosystems). The two synthetic oligonucleotides are shown above in (SEQ ID NO:3) and (SEQ ID NO:4), except for the 5 dCTP bases that were added to the 5' end of each to facilitate cutting with restriction enzymes.

Codon usage may be optimized for high level expression in an expression system. Suitable expression systems include: yeast, eukaryotic viral expression systems such as Baculovirus or Vaccinia virus and *E. coli*. The preferred expression system is *E. coli* BL21(DE3). The oligonucleotides are purified by affinity chromatography, preferably using NENSORB columns (DUPONT), annealed, filled in with dNTPs using SEQUENASE (U.S. BIOCHEMICAL), and digested with restriction enzymes using standard techniques. The resulting fragment is gel-purified, preferably using NUSIEVE (FMC BIOPRODUCTS) and ligated into a suitable plasmid such as pCSP105, a variant of pSR9, using standard techniques as described in Ausubel et al., eds. (1989) *Current Protocols in Molecular Biology*, John Wiley & Sons, Inc., New York. The resulting construct, encoding a fusion protein of T7 gene 9 and MgTX separated by a factor $X_a$ cleavage site may be verified using dideoxy sequencing.

The expression plasmid is used to transform *E. coli* BL21 (DE3) which are subsequently induced to produce the MgTX fusion protein by treatment with IPTG while the *E. coli* are in log phase growth. The cells are then harvested, washed, broken by sonication and the MgTX fusion protein can be verified by SDS-PAGE. The recombinant MgTX is cleaved from its fusion protein using Factor Xa protease. Recombinant MgTX may be separated and purified according to the procedures used for isolating MgTX from crude venom.

The coding strand of the DNA from the MgTX plasmid including SalII, Factor $X_a$, MgTX, and Hind III is shown below: (SEQ ID NO:5)

5' GTCGACGGAT CCATCGAAGG TCGTACCATC ATCAACGTTA

AATGCACCTC TCCGAAACAG TGCCTGCCGC CGTGCAAAGC

TCAGTTCGGT CAGTCTGCTG GTGCTAAATG CATGAACGGT

AAATGCAAAT GCTACCCGCA CTGATAGGAA GCTT 3'

The present invention is also directed to a method for suppressing the immune system in a subject in need of such treatment comprising the administration to a subject in need of such treatment of a nontoxic immunosuppressant amount of Margatoxin. Specifically, the method of this invention is useful in treating and preventing the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

Margatoxin is also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne, Alopecia areata, eosinophilic fasciitis, and atherosclerosis.

Margatoxin is further useful in the treatment of respiratory diseases, for example: sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyper-reponsiveness), bronchitis and the like. MgTX may also be useful for treating hepatic injury associated with ischemia.

MgTX may also be indicated in certain eye diseases such as keratoconjunctivitis, vernal conjunctivitis, uveitis associated with Behcet's disease, keratitis, herpetic keratitis, conical cornea, dystorphia epithelialis corneae, corneal leukoma, ocular pemphigus, Mooren's ulcer, Scleritis, Graves' ophthalmopathy, severe intraocular intimation, and the like. MgTX is also useful for treating multidrug resistance of rumor cells, (i.e. enhancing the activity and/or sensitivity of chemotherapeutic agents), preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g., Crohn's disease and ulcerative colitis), necrotizing enterocolitis), or intestinal lesions associated with thermal burns, cytomegalovirus infection, particularly HCMV infection.

Further, MgTX is also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy. Further still, MgTX may be used in the treatment of diseases including intestinal inflammations/allergies such as Coeliac disease, proctitis, eosinophilic gastroenteritis, mastocytosis, Crohn's disease and ulcerative colitis; and food-related allergic diseases which have symptomatic manifestation remote from the gastrointestinal tract, for example migraine, rhinitis and eczema.

MgTX may also be useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The Margatoxin peptide may be administered intranasally, intravenously, subcutaneously or intramuscularly, preferably intraveneously. Administration may occur one to four times daily or less frequently at therapeutically effective doses. Margatoxin may also be administered on an intermittent basis when therapeutically advisable. Dosages may be varied, depending on the age, and other conditions of patients, but daily dosage for adults is within a range of from about 0.001 mg to 10 mg, preferably 0.1 mg to 1.0 mg which may be given in a single dose or two or more divided dosages. Higher dosages may be favorably employed as required.

Margatoxin, either isolated from the venom of *Centruorides margaritatus* or produced by recombinant DNA technology or other means, is formulated as an injectable formulation, preferably an intravenous injection. The formulation may be formulated as either a suspension or a solution. A suspension may have the advantage of providing more gradual release of the active agent. The suspensions or solutions of the formulation of the present invention contain 0.01% to 10% Margatoxin, preferably 0.1 to 1%, in a pharmaceutically acceptable carrier.

When Margatoxin is administered as an injectable suspension or solution, the suspension or solution comprises Margatoxin and a suitable pharmaceutical carrier. Injectable suspensions and solutions may be formulated according to known art, using suitable nontoxic, parenterally acceptable diluents or solvents, such as 1,2-propanediol, water, Ringer's solution, dextrose solution or isotonic sodium chloride solution. These injectable suspensions or solutions may further contain excipients suitable for manufacture of aqueous suspensions and solutions. Such excipients may be:

(1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be:
  (a) a naturally occurring phosphatide such as lecithin,
  (b) a condensation product of any alkylene oxide with a fatty acid, for example, polyoxyethylene stearate,
  (c) a condensation product of an ethylene oxide with a long chain aliphatic alcohol, for example, heptadecaethyleneoxycetanol,
  (d) a condensation product of ethylene oxide with a partial ester derived from a fatty acid and hexitol such as polyoxyethylene sorbital monooleate, or
  (e) a condensation product of ethylene oxide with a partial ester derived from a fatty acid and hexitol anhydride, for example, polyoxyethylene sorbital monooleate.

Such suspensions and solutions may further contain microcrystalline cellulose for imparting bulk and methylcellulose as a viscosity enhancer.

The aqueous suspensions and solutions may also contain one or more preservatives, for example, ethyl or n-propyl p-hydroxybenzoate, and antioxidants and the like may be incorporated as required.

In addition, the aqueous suspension or solution may, if necessary, be buffered to a physiologically appropriate pH by the addition of a suitable buffer such as sodium acetate, sodium lactate, sodium benzoate or Tris.

Dispersible powders and granules are suitable for the preparation of an aqueous suspension. They provide the active ingredient in a mixture with a dispersing or wetting agent, a suspending agent and one or more preservatives. Suitable dispersing or wetting agents and suspending agents are exemplified by those already mentioned above. Additional excipients may also be present.

An oily suspension may be formulated by suspending the active ingredient in a vegetable oil, for example: arachis oil, olive oil, sesame oil, or coconut oil, or in a mineral oil such as liquid paraffin. The oily suspensions may contain a thickening agent, for example: beeswax, hard paraffin or cetyl alcohol. These compositions may be prepared by the addition of an antioxidant such as ascorbic acid.

The formulation of the present invention may be used in conjunction with modem auto-injection devices which increase the convenience and decrease the discomfort of subcutaneous injections. The use of the formulation of the present invention with such autoinjection devices may increase patient compliance by improving ease of administration.

The following examples are given for the purpose of illustrating the present invention and shall not be construed as being limitations on the scope or spirit of the invention.

EXAMPLE 1

Purification of Margatoxin Peptide (MgTX)

Crude lyophilized venom of the scorpion *C. margaritatus* obtained from MILLER INTERNATIONAL VENOMS, P.O. Box 1644, Hollywood, Fl. 33022, was suspended in 20 mM Na-borate, pH 9.0, at a concentration of 5 mg/mL. After agitating the venom by vortex, the suspension was clarified by centrifugation at 27,000× g for 15 min. The supernatant was removed, filtered through a MILLEX-GV filter (0.2 μm pore size; MILLIPORE) and loaded onto a MonoS FPLC column (HR5/5; PHARMACIA), equilibrated with 20 mM sodium borate, pH 9.0. After the absorbance of the eluate had returned to baseline, bound material was eluted from the resin with a linear gradient of NaCl (0.75 M/hr) at a flow rate of 0.5 mL/min. Fractions were separated and assayed for their ability to inhibit [$^{125}$I]ChTX binding to either rat brain synaptic plasma membranes or bovine aortic smooth muscle sarcolemmal membranes. [$^{125}$I]ChTX was obtained from New England Nuclear Corporation. Fractions that blocked [$^{125}$I]ChTX binding only to brain membranes and that displayed the highest absorbance at 280 nm were considered for further characterization. Fractions eluting at 210–340 mM NaCl displayed inhibitory activity against [$^{125}$I]ChTX binding to $K_v1.3$ in rat brain membranes. These fractions were loaded onto a 300 Å pore size $C_{18}$ reversed phase HPLC column (0.46×25 cm) that had been equilibrated with 10 mM trifluoroacetic acid (TFA). The column was eluted with a linear gradient of isopropyl alcohol/acetonitrile (2:1; 0–15%, 33 minutes) at a flow rate of 0.5 mL/min. Fractions were collected, lyophilyzed and later reconstituted with 100 mM NaCl, 20 mM Tris-HCl, pH 7.4. Inhibitory binding activity was quantitatively recovered. This material elutes at ca. 10% organic solvent and appears chromatographically pure. Samples were denatured in the presence of SDS and applied to precast 16% Tricine gels (NOVEX). The SDS-PAGE analysis of the active material using silver staining revealed a single component with an apparent molecular mass of ca. 4 kDa.

EXAMPLE 2

Amino Acid Sequence Determination of MgTX

Purified MgTX, obtained above, was reduced, subjected to alkylation with iodoacetic acid and repurified by reverse-phase chromatography as previously described for ChTX in Gimenez-Gallego et al. *Proc. Natl. Acad. Sci. U.S.A.* 85, 3329, 1988. Briefly, purified MgTX was reduced in a medium consisting of 6M guanidine-HCl, 0.1% EDTA $Na_2$, 0.1M Tris-HCl, pH 9.5, 20 mM DTT by incubation at 50° C. for two hours in the dark. Alkylation was then carded out in a medium consisting of 6M guanidine-HCl, 1.0% EDTA $Na_2$, 0.7M Tris-HCl, pH 7.8, 120 mM iodoacetic acid for 40 minutes at room temperature. The reaction mixture was applied to a $C_{18}$ reversed phase column as employed for the purification of MgTX. Elution took place by applying a linear gradient of isopropyl alcohol/acetonitrile (2:1, 0–30%, 30 minutes). Approximately 0.5 nmoles of reduced-alkylated toxin was loaded onto a PORTON peptide support filter and Edman degradation was performed using a PORTON 2090 microsequencer. Phenylthiohydantoin derivatives were analyzed using an on-line detection system. Typical repetitive yields from at least six sequencing runs were 94%.

The primary amino acid sequence of MgTX is shown below: (SEQ ID NO:1).

Thr—Ile—Ile—Asn—Val—Lys—Cys—Thr—Ser—Pro—Lys—Gln—Cys—Leu—Pro—Pro—
                  5                    10                15

Cys—Lys—Ala—Gln—Phe—Gly—Gln—Ser—Ala—Gly—Ala—Lys—Cys—Met—Asn—Gly—
                20                  25                30

Lys—Cys—Lys—Cys—Tyr—Pro—His
             35

Because of the presence of several Proline residues, link steps were used at those positions to increase the efficiency of the cleavage reaction. From these data obtained in repetitive runs, 38 amino acid residues were well-defined. However, from our experience sequencing other peptides, we noted that the last residue of a peptide is frequently lost from the filter support and, in most cases, cannot be identified by this technique. Therefore, the molecular mass of MgTX was determined by electrospray mass spectroscopy. Mass spectral analysis of MgTX showed that the predominant component present in the preparation has a mass of 4178.0 Da. Since the combined mass of the 38 amino acid residues defined by sequence analysis only accounts for 4042.6 Da, we concluded that the carboxyl terminus of MgTX had not been identified. The difference in mass, 135.4, suggested histidine as the most likely candidate for the carboxyl terminal residue.

To resolve this issue, a sample of purified MgTX was subjected to amino acid hydrolysis. A sample containing 1 nmol of purified MgTX was subjected to acid hydrolysis, derivatized and phenylthiocarbamyl amino acid derivatives identified by reversed-phase chromatography using a PICO-TAG (WATERS) system. The absorbance spectrum of purified MgTX was digitized in a BECKMAN DU 7400 UV/Vis spectrophotometer. Protein extinction coefficients were calculated by determining the amino acid composition of an aliquot of MgTX and then correlating protein content with the recorded absorbance at 280, 235, and 215 nm, respectively. The result of this experiment is shown in Table I below.

TABLE I

Amino Acid Analysis of Margatoxin

|  | Residues/mol Toxin | |
| --- | --- | --- |
|  | Observed | Integer |
| Aspartic acid or asparagine | 1.80 | 2 |
| Glutamic acid or glutamine | 3.00 | 3 |
| Serine | 2.05 | 2 |
| Glycine | 3.15 | 3 |
| Histidine | 0.98 | 1 |
| Arginine | ND[a] |  |
| Threonine | 1.97 | 2 |
| Alanine | 3.01 | 3 |
| Proline | 4.05 | 4 |
| Tyrosine | 1.02 | 1 |
| Valine | 1.02 | 1 |
| Methionine | 0.93 | 1 |
| Cysteine | 5.92 | 6 |
| Isoleucine | 1.64 | 2 |
| Leucine | 1.00 | 1 |
| Phenylalanine | 1.04 | 1 |
| Lysine | 5.94 | 6 |

ND[a], not detected

The amino acid composition of MgTX corresponded well with that expected from the amino acid sequence determination, and, in addition, the presence of a single His residue was detected. These data defined MgTX as a 39 amino acid peptide with a carboxyl terminal histidine. The extinction coefficients determined for MgTX were: 12.82 cm$^{-1}$ × (mg/ml)$^{-1}$ at 215 nm, 2.59 cm$^{-1}$ ×(mg/ml)$^{-1}$ at 235 nm, and 0.27 cm$^{-1}$ × (mg/ml)$^{-1}$ at 280 nm.

EXAMPLE 3

Competition binding of MgTX to K$_v$1.3 in rat brain synaptic plasma membrane vesicles, and to Maxi K channels in bovine aortic smooth muscle sarcolemmal membranes The potency of MgTX as an inhibitor of [$^{125}$I]ChTX binding to K$_v$1.3 was evaluated. The binding of [$^{125}$I]ChTX to either rat brain synaptic plasma membrane vesicles (K$_v$1.3 channel; Vazquez et al., *J. Biol. Chem.* 265, 15564, 1990) or bovine aortic smooth muscle sarcolemmal membranes (Maxi-K channel; Vazquez et al., *J. Biol. Chem.* 264, 20402, 1989) was determined as described. Briefly, membrane vesicles were incubated with [$^{125}$I]ChTX in the presence or absence of other added agents, until equilibrium was achieved. Separation of bound from free ligand was accomplished by filtration through GF/C glass fiber filters (WHATMAN) that had been presoaked in 0.5% polyethyleneimine. Nonspecific binding was determined in the presence of 10 nM unlabeled ChTX. Data from saturation experiments were analyzed in a Scatchard representation to determine K$_d$ and B$_{max}$ values. Triplicate samples were obtained for each experimental point and the data were averaged. The standard deviation of the mean was typically less than 2%. MgTX inhibited [$^{125}$I]ChTX binding to brain membranes in a concentration-dependent fashion with a Hill coefficient of 1.7 and an IC$_{50}$ of 36 pM, under the low ionic strength conditions (50 mM NaCl, 20 mM Tris-HCl, pH 7.4) used in this assay. As an indication of selectivity, MgTX had no effect on [$^{125}$I]ChTX binding to the Maxi-K channel in smooth muscle membranes at concentrations up to 10 nM. Saturation binding experiments employing increasing concentrations of [$^{125}$I]ChTX in the presence of fixed amounts of MgTX indicated that the inhibition of ChTX binding was due to a mixed effect on ligand affinity and receptor density. Under control conditions, [$^{125}$I]ChTX was bound to a single class of sites with a K$_d$ of 31 pM and a maximum density of 0.43 pmol/mg protein. In the presence of 25 pM MgTX, the K$_d$ for [$^{125}$I]ChTX increased to 52 pM, while the receptor density diminished to 0.34 pmol/mg protein. Thus, it appears that MgTX does not behave as a strictly competitive inhibitor of ChTX binding to K$_v$1.3 in rat brain.

EXAMPLE 4

Competition Binding of MgTX to K$_v$1,3 of Human T Lymphocytes

In addition to being tested for competition for [$^{125}$I]ChTX binding to rat brain and bovine aortic smooth muscle, MgTX was evaluated for its effects on [$^{125}$I]ChTX binding to human T lymphocytes and to plasma membranes prepared from Jurkat cells, a human T-cell leukemia line. MgTX competition for [$^{125}$I]ChTX binding to human T cells was performed as described by Lin, et al., *J. Exp. Med.* 177, 637–645, 1993. Binding experiments using monocyte-depleted, E-rosetted human T cells were carried out in isotonic sucrose with 5 mM KCl, 5 mM NaCl, 6 mM glucose and 10 mM HEPES, pH 8.0 until equilibrium was achieved. The procedure for binding to plasma membranes from Jurkat Cells is similar except that the binding solution was 3 mM KCl, 7 mM NaCl, 10 mM HEPES, pH 8.0. Free ligand was removed from bound by filtration through Whatman GF/C glass fiber filters (pretreated with 0.5% polyethylenimine). [$^{125}$I]ChTX binding was completely inhibited by MgTX with IC$_{50}$'s of 1.4 and 2.7 pM for human T cells and plasma membranes from Jurkat cells, respectively. Hill coefficients were 2 in both cases.

EXAMPLE 5

Expression of Recombinant MgTX

In order to verify that the amino acid sequence determined for MgTX corresponds to the active component of the preparation, as well as to obtain significant quantities of the peptide, recombinant MgTX (rMgTX) was expressed in *E. coli* as part of a fusion protein with the T7 gene 9 product. After partial purification of the fusion protein and cleavage with factor X$_a$ protease, rMgTX was purified to homogeneity by ion-exchange and reversed-phase chromatography. Amino acid analysis and sequence determination indicated that rMgTX is identical to native peptide. Importantly, rMgTX displayed the same potency and selectivity as an inhibitor of K$_v$1.3 (see Example 8 below). In addition, rMgTX displayed the same potency as native MgTX for inhibition of [$^{125}$I]ChTX binding to brain membranes, and did not affect ChTX binding to the Maxi-K channel. These results indicate that the active species of the purified preparation corresponds to MgTX, and not to some other minor peptidyl component. Moreover, the carboxyl terminus of MgTX does not require amidation for full biological activity of the peptide.

EXAMPLE 6

Construction of the Margatoxin Plasmid

The MgTX gene was constructed using two synthetic oligonucleotides that were synthesized using an ABI model 391 DNA synthesizer (Applied Biosystems). The two synthetic oligonucleotides are shown below, except for the 5 dCTP bases that were added to the 5' end of each to facilitate cutting with restriction enzymes. (SEQ ID NO:3),

5' GTCGACGGAT CCATCGAAGG TCGTACCATC ATCAACGTTA

AATGCACCTC TCCGAAACAG TGCCTGCCGC CGTGCAAAGC TCAG 3'

(SEQ ID NO: 4)

5' GGCACGTTTC GAGTCAAGCC AGTCAGACGA CCACGATTTA

CGTACTTGCC ATTTACGTTT ACGATGGGCG TGACTATCCT TCGAA3'

The two sequences above were combined to produce the gene having the coding strand shown below: (SEQ. ID NO:5)

5' GTCGACGGAT CCATCGAAGG TCGTACCATC ATCAACGTTA

AATGCACCTC TCCGAAACAG TGCCTGCCGC CGTGCAAAGC

TCAGTTCGGT CAGTCTGCTG GTGCTAAATG CATGAACGGT

AAATGCAAAT GCTACCCGCA CTGATAGGAA GCTT 3'

Codon usage was optimized for high level expression in *E. coli*. The oligonucleotides were purified using NENSORB columns (DUPONT), annealed, filled in with dNTPs using SEQUENASE (U.S. BIOCHEMICAL), and digested with restriction enzymes using standard techniques. The resulting fragment was gel purified using NUSIEVE (FMC BIO-PRODUCTS) and ligated into plasmid pCSP105, a variant of pSR9 using standard techniques as described in Ausubel et al., eds. (1989) *Current Protocols in Molecular Biology*, John Wiley & Sons, Inc., New York. The resulting construct, encoding a fusion protein of T7 gene 9 and MgTX separated by a factor X$_a$ cleavage site was verified using dideoxy sequencing.

EXAMPLE 7

Expression and Purification of Recombinant Margatoxin

*E. coli* BL21 (DE3) harboring p6MgTX were cultured and induced with IPTG. Purification of the fusion protein was done essentially as described in Park, et al. *Proc. Natl. Acad. Sci. U.S.A.* 88, 2046, 1991. Briefly, induced cells were pelleted at 4,000× g for 10 minutes, washed once in 50 mL of phosphate buffered saline and stored overnight at −80° C. Cells were thawed on ice and resuspended in 20 mL of 10 mM Tris-HCl, pH 8.0, 50 mM NaCl, 1 mM Na$_2$EDTA, 1 mM DTT and protease inhibitors (100 µM PMSF, 1 µg/mL pepstatin, 1 µg/mL leupeptin), and incubated with 0.5 mg/mL lysozyme. Cells were disrupted by sonication and the lysate was centrifuged at 27,000× g for 15 min. After removal of nucleic acids with streptomycin sulphate, the lysate was loaded onto a DEAE-SEPHAROSE column equilibrated in 10 mM Tris-HCl, pH 8.0, 50 mM NaCl, 1 mM DTT. After washing the column, the fusion protein was eluted with 350 mM NaCl, 10 mM Tris-HCl, HCl, pH 8.0, 1 mM DTT. Fractions containing the fusion protein were identified by Coomassie staining of SDS-PAGE gels, combined, and dialyzed overnight against 20 mM Tris-HCl, 100 mM NaCl, 0.5 mM β-mercaptoethanol, pH 8.3. $CaCl_2$ was then added to a final concentration of 3 mM, and 1 µg Factor $X_a$ was added per 200 µg of fusion protein. The digestion mixture was incubated at room temperature for 18 hours. The recombinant MgTX (rMgTX) was purified from the cleavage mixture using MonoS FPLC and $C_{18}$ reversed phase HPLC columns as described in EXAMPLE 1 for native MgTX. The yield was 3–4 mg of purified rMgTX per liter of culture. The composition of the purified material was verified by Edman degradation and amino acid hydrolysis.

EXAMPLE 8

Electrophysiological measurements

Ionic currents were recorded from human peripheral T-lymphocytes using the whole cell patch clamp technique described in Cahalan, M. and Neher, E., *Meth. Enzymol.* 207, 3, 1992. Purified human T cells were obtained as described in Leonard et al., *Proc. Natl. Acad. Sci. U.S.A.*, 89, 10094, 1992, and recordings were carried out in a bath solution consisting of $^{125}$ mM NaCl, 2.5 mM KCl, 1.0 mM $CaCl_2$, 2.0 mM $MgCl_2$, 10 mM HEPES (potassium salt), 10 mM glucose, 5 mM Na-pyruvate, and 0.05% BSA. The pH was adjusted to 7.2, and experiments were performed at room temperature (19°–22° C.). The intracellular (pipette) solution contained 140 mM K-glutamate, 1 mM $MgCl_2$, 10 mM HEPES (potassium salt), and 0.1 mM EGTA. The pH was adjusted to 7.2. Patch pipettes were fabricated from DAGAN (Minneapolis, Minn.) LG-16 glass and had resistances of 2 to 8MΩ. Currents were measured using a DAGAN model 3900 patch clamp. Delivery of command voltages, data acquisition, and post-acquisition analysis were aided by a microcomputer running the Pclamp program suite (AXON INSTRUMENTS, Foster City, Calif.).

Ionic currents were also recorded from Xenopus oocytes that had been injected with RNA transcribed in vitro from one or another of the following $K^+$ channel cDNA clones. $K_v1$ (rat $K_v1.5$), rat or human $K_v3$ (rat $K_v1.3$; human $K_v1.3$), $K_v4$ (rat $K_v3.1$), rat ISK, $K_v2$ (rat $K_v1.6$) or Drosophila Shaker-H4. The names of the clones are listed as originally published, with the appropriate parenthetical designation according to the unified gene nomenclature proposed by Chandy. Shaker-H4 is a splice variant from the original Drosophila Shaker $K^+$ channel gene. $K_v1.3$ is the ChTX-sensitive delayed rectifier current found in rat and human T lymphocytes (data from rat and human clones were indistinguishable and were combined) and it is a member of the Shaker family. $K_v1.5$ is a channel cloned from rat (Swanson et al., *Neuron*, 4, 929, 1990) and is another member of the Shaker family. The $K_v1.5$ transcript has been detected in pancreatic β cells as described in Philipson, et al., *Proc. Natl. Acad. Sci. U.S.A.* 88, 53, 1991. $K_v1.6$ is a clone from rat (Swanson et al., *Neuron*, 4, 929, 1990) that shows 86% homology with $K_v1.3$. Unlike $K_v1.3$, this channel is very insensitive to ChTX, with an $IC_{50}$>1 µM. It is another member of the Shaker family. $K_v3.1$ is a channel cloned from rat (Luneau et al., *Proc. Natl. Acad. Sci. U.S.A.* 88, 3932, 1991) that appears to encode a ChTX-insensitive delayed rectifier found in thymic cells (the l-current) (Chandy et al., *Biophys. J.*, 61, A257, 1992)). It is a member of the Shaw subfamily. ISK is a slowly-activating $K^+$ channel cloned from smooth muscle and heart (Folander et al., *Proc. Natl. Acad. Sci. U.S.A.*, 87, 2975, 1990). This channel appears to underlie the $I_{Ks}$ delayed rectifier in heart muscle (Sanguinetti and Jurkiewitz, *Am. J. Physiol.*, 260. J393. 1991; Sanguinetti and Jurkiewitz, *J. Gen. Physiol.*, 96, 195, 1990). It is structurally unrelated to the other voltage-activated $K^+$ channel clones. The ISK transcript has been detected in lymphocytes (Attali et al., *J. Biol. Chem,.* 267, 8650, 1992), but no evidence of the $I_{Ks}$ current has been found in those cells.

Methods for oocyte isolation and micro-injection were previously described in Goldin, *Meth. Cell Biol*, 36, 487, 1991, and Swanson and Folander, *Meth. Enzymol.*, 207, 310, 1992. Currents expressed in oocytes were measured using a DAGAN model CA-1 two-electrode voltage clamp. Delivery of command voltages, data acquisition and post-acquisition analysis were aided by a microcomputer running the Pclamp program suite. The oocyte bathing solution consisted of 96 mM NaCl, 2.5 mM KCl, 1 mM $MgCl_2$, 1.8 mM $CaCl_2$, 10 mM HEPES, and 0.05% BSA. The pH was 7.2. All recordings were obtained at room temperature (19°–22° C.). The intracellular microelectrodes were fabricated from DAGAN LE-16 glass in a two-stage pull to a final resistance of 0.6 to 2MΩ and filled with 3M KCl. For both lymphocyte and oocyte experiments, peptides were diluted into the extracellular solution from 20 µM aqueous stock containing 100 mM NaCl. The presence of 0.05% BSA in the bath solution inhibited non-specific loss of dilute peptide toxins in the perfusion tubing.

Both native and recombinant MgTX were tested for their ability to block voltage gated $K^+$ channels. The two preparations gave identical results on $K_v1.3$. There was insufficient native toxin to carry out selectivity studies, so those were conducted using the recombinant material exclusively. Complete inhibition of the voltage activated $K^+$ channel from human lymphocytes occurs at 1 nM, and recovery from block, following removal of MgTX from the bath, proceeds slowly, with a $t_{1/2}$ of >20 minutes. The apparent $IC_{50}$ for inhibition of the lymphocyte $K_v1.3$ current is between 20 to 100 pM. This is five to ten-fold more potent than ChTX on the same preparation. As reported previously, MgTX has no effect on three different ChTX-sensitive, $Ca^{2+}$-activated $K^+$ channels of lymphocytes, even at 100 nM (Leonard et al., *Proc. Natl. Acad. Sci. U.S.A.* 89, 10094, 1992).

Of the six cloned channels tested, three ($K_v5$, $K_v3.1$, and ISK) were completely insensitive to 200 nM MgTX. The most sensitive channel is $K_v3$, with an $IC_{50}$ of ~30 pM. The next most sensitive channel, $K_v1.6$, was half blocked at 5 nM, while Shaker-H4 displayed an $IC_{50}$ of 100 nM.

EXAMPLE 9

Iodination of Margatoxin

Two reaction mixtures were prepared in individual microcentrifuge tubes (1.5 mL), each containing the following (in a total volume of 0.065 mL): ENZYMOBEADS$^R$ (the contents of a single reaction vial, rehydrated according to the manufacturer's instructions), 200 mM sodium phosphate, pH 7.0, and 30.8 µM recombinant MgTX. The reaction mixtures were allowed to equilibrate at room temperature for approximately 15 minutes. Then, Na$^{125}$I (2 mCi; approx. 6 µL) was added to each tube, followed by a solution of β-D-glucose (5 µL of a 50 mg/mL solution in water). The contents of the tubes were mixed by gentle tapping. Incubation was for 20 min at room temperature. The tubes were then opened and allowed to vent for 1 min. The reaction mixtures were filtered on a COSTAR microcentrifuge filter (0.22 μm). Each tube was washed with sodium phosphate, pH 7.0 (0.15 mL) and the washes centrifuged through the same filter as the reaction mixtures. Finally, the filter was washed with buffer (0.075 mL). The reaction supernatants and washes were combined and loaded onto a VYDAC C18 Protein & Peptide column (0.46×25 cm) that had been equilibrated at room temperature with 5% solvent B(2:1 isopropanol:acetonitrile, 4 mM trifluoroacetic acid)/95% solvent A (10 mM trifluoroacetic acid). After unreacted sodium iodide had been eluted by washing the column with the equilibration solvent for 25 min at 0.8 mL/min, the unreacted MgTX and its iodinated products were separated by a linear gradient of (9–15)% solvent B over a period of 30 min. Two protein peaks containing radioactivity were detected. The second, smaller peak (Diiodinated margatoxin) was used in the binding assay.

EXAMPLE 10

Competition binding of MgTX to $K_v1.3$ of human T lymphocytes

Diiodinated margatoxin, $[^{125}I]_2MgTX$, was used to develop binding assays for $K_v1.3$ in human T lymphocytes and in plasma membranes prepared from Jurkat cells. $[^{125}I]_2MgTX$ was incubated either with intact monocyte-depleted, e-rosetted human peripheral blood T lymphocytes or with Jurkat plasma membranes in a solution containing 4.6 mM KCl, 106 mM NaCl, 20 mM HEPES, pH 7.4 until equilibrium was reached. Experiments in cells were performed at ambient temperature (from 21° to 25° C.) while the plasma membranes were incubated at 37° C. Free $[^{125}I]_2MgTX$ was removed from bound by passing the reaction mixture through WHATMAN GF/C glass fiber filters which had been presoaked with 0.5 % polyethylenimine. The radioactivity trapped on these filters was determined using gamma-counting techniques. When this procedure was used for $[^{125}I]_2MgTX$ binding to Jurkat plasma membranes, the equilibrium constant $(K_d)$ was 8 pM and maximum binding $(B_{max})$ was 64 fmol per mg protein. $[^{125}I]_2MgTX$ binding to human T cells exhibited a $K_d$ of 15 pM and a $B_{max}$ of 800 sites/cell.

EXAMPLE 11

Formulation of Margatoxin
An injectable formulation is prepared as follows:

| | |
|---|---|
| Margatoxin | 1 mg |
| Polysorbate 80 | 10 μg |
| Sodium chloride | 10 mg |
| Distilled water for injection | q.s. |
| per vial of 1 mL | |

The formulation is filtered to remove organisms and dispensed into a 2 mL glass vial.

While the foregoing specification teaches the principles of the present invention, with examples provided for the purpose of illustration, it will be understood that the practice of the invention encompasses all of the casual variations, adaptations, modifications, deletions or additions of procedures and protocols described herein, as come within the scope of the following claims and its equivalents.

What is claimed is:

1. A purified peptide consisting of the sequence (SEQ ID NO:1):

Thr—Ile—Ile—Asn—Val—Lys—Cys—Thr—Ser—Pro—Lys—
       5                              10

Gln—Cys—Leu—Pro—Pro—Cys—Lys—Ala—Gln—Phe—
        15                            20

Gly—Gln—Ser—Ala—Bly—Ala—Lys—Cys—Met—Asn—
        25                            30

Gly—Lys—Cys—Lys—Cys—Try—Pro—His.

2. The purified peptide of claim 1 wherein the peptide is produced by recombinant techniques.

3. The purified peptide of claim 1 wherein the peptide is produced by recombinant techniques using *E. coli* cells.

4. A pharmaceutical composition comprising an immunosuppressive amount of the peptide of claim 1 and a pharmaceutically acceptable carrier.

5. An injectable pharmaceutical composition comprising 0.001% to 10% (w/v) of the peptide of claim 1 and a pharmaceutically acceptable carrier.

6. The injectable pharmaceutical composition of claim 5 wherein the carrier comprises aqueous sodium chloride.

7. A method of suppressing the immune system in a mammalian subject in need of such treatment comprising the administration of a therapeutically effective amount of the peptide of claim 1 to the subject.

8. A method for the treatment of resistance to transplantation comprising the administration to a mammal in need of such treatment of an effective amount of the peptide of claim 1.

9. A radiolabelled peptide according to claim 1.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: NO     ( v i ) ORIGINAL SOURCE:
        ( A ) ORGANISM: CENTRUROIDES MARGARITATUS     ( x i ) SEQUENCE DESCRIPTION: SEQ ID NO:1:

```
Thr  Ile  Ile  Asn  Val  Lys  Cys  Thr  Ser  Pro  Lys  Gln  Cys  Leu  Pro  Pro
 1                    5                        10                       15

Cys  Lys  Ala  Gln  Phe  Gly  Gln  Ser  Ala  Gly  Ala  Lys  Cys  Met  Asn  Gly
                     20                       25                       30

Lys  Cys  Lys  Cys  Tyr  Pro  His
                35
```

( 2 ) INFORMATION FOR SEQ ID NO:2:

( i ) SEQUENCE CHARACTERISTICS:
        ( A ) LENGTH: 120 base pairs 5,494,895

(B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

```
ACCATCATCA ACGTTAAATG CACCTCTCCG AAACAGTGCC TGCCGCCGTG CAAAGCTCAG    60
TTCGGTCAGT CTGCTGGTGC TAAATGCATG AACGGTAAAT GCAAATGCTA CCCGCACTGA   120
```

(2) INFORMATION FOR SEQ ID NO:3:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

```
GTCGACGGAT CCATCGAAGG TCGTACCATC ATCAACGTTA AATGCACCTC TCCGAAACAG    60
TGCCTGCCGC CGTGCAAAGC TCAG                                           84
```

(2) INFORMATION FOR SEQ ID NO:4:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

```
GGCACGTTTC GAGTCAAGCC AGTCAGACGA CCACGATTTA CGTACTTGCC ATTTACGTTT    60
ACGATGGGCG TGACTATCCT TCGAA                                          85
```

(2) INFORMATION FOR SEQ ID NO:5:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GTCGACGGAT CCATCGAAGG TCGTACCATC ATCAACGTTA AATGCACCTC TCCGAAACAG    60
TGCCTGCCGC CGTGCAAAGC TCAGTTCGGT CAGTCTGCTG GTGCTAAATG CATGAACGGT   120
AAATGCAAAT GCTACCCGCA CTGATAGGAA GCTT                               154
```